United States Patent
Lee

(10) Patent No.: US 10,335,564 B2
(45) Date of Patent: Jul. 2, 2019

(54) SYSTEM AND METHOD FOR CONTROLLING EXSUFFLATION PRESSURE DURING IN-EXSUFFLATION

(71) Applicant: KONINKLIJKE PHILIPS N.V., Eindhoven (NL)

(72) Inventor: Seunghyun Lee, Spring Hill, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 604 days.

(21) Appl. No.: 15/022,602

(22) PCT Filed: Sep. 5, 2014

(86) PCT No.: PCT/IB2014/064268
§ 371 (c)(1),
(2) Date: Mar. 17, 2016

(87) PCT Pub. No.: WO2015/040520
PCT Pub. Date: Mar. 26, 2015

(65) Prior Publication Data
US 2016/0228660 A1 Aug. 11, 2016

Related U.S. Application Data

(60) Provisional application No. 61/879,759, filed on Sep. 19, 2013.

(51) Int. Cl.
*A61M 16/00* (2006.01)
*A61B 5/087* (2006.01)
(Continued)

(52) U.S. Cl.
CPC ......... *A61M 16/0003* (2014.02); *A61B 5/087* (2013.01); *A61B 5/091* (2013.01);
(Continued)

(58) Field of Classification Search
CPC ............ A61M 16/003; A61M 16/0051; A61M 16/0009; A61M 16/00; A61M 16/161;
(Continued)

(56) References Cited

U.S. PATENT DOCUMENTS 3,991,304 A * 11/1976 Hillsman ............... A61B 5/087
600/538
5,921,238 A 7/1999 Bourdon
(Continued)

FOREIGN PATENT DOCUMENTS

EP 2165726 A2 3/2010
EP 2246087 A1 3/2010
WO WO2012085787 A2 6/2012

*Primary Examiner* — Justine R Yu
*Assistant Examiner* — Matthew Ryan Moon
(74) *Attorney, Agent, or Firm* — Michael W. Haas

(57) ABSTRACT

A system and method to in-exsufflate a subject is described. The system provides an effective non-invasive alternative to invasive treatments such as a tracheostomy for ALS patients. The system detects airway collapse during exsufflation and adjusts in-exsufflation therapy settings to minimize airway collapse, thus maximizing the efficacy of the in-exsufflation therapy. In some embodiments, tidal volume, tidal flow rate, and/or other parameters are monitored during in-exsufflation. Exsufflation pressure is adjusted based on the monitored parameters to maintain an open airway during exhalation of the subject. Exsufflation pressure is adjusted based on a comparison of an actual exhalation tidal volume to a target exhalation tidal volume, an actual exhalation flow rate to a target exhalation flow rate, an actual inhalation tidal volume to a target inhalation volume, and/or other comparisons.

15 Claims, 5 Drawing Sheets

(51) Int. Cl.
*A61B 5/091* (2006.01)
*A61M 16/10* (2006.01)
*A61M 16/16* (2006.01)

(52) U.S. Cl.
CPC .... *A61M 16/0009* (2014.02); *A61M 16/0051* (2013.01); *A61M 16/0066* (2013.01); *A61M 16/161* (2014.02); *A61M 2016/0018* (2013.01); *A61M 2016/0027* (2013.01); *A61M 2016/0036* (2013.01); *A61M 2016/102* (2013.01); *A61M 2205/332* (2013.01); *A61M 2205/3331* (2013.01); *A61M 2205/3368* (2013.01); *A61M 2205/52* (2013.01); *A61M 2230/005* (2013.01); *A61M 2230/42* (2013.01)

(58) Field of Classification Search
CPC ........... A61M 2230/42; A61M 2230/432–435; A61M 2230/005; A61M 2016/102; A61M 2016/003–0042; A61M 2016/1025–103; A61M 2016/0018; A61M 2016/0036; A61M 2016/0027; A61M 2205/3334; A61M 2205/3344; A61M 2205/332; A61M 2205/3368; A61M 2205/3331; A61M 2205/52; A61M 16/0066; A61B 5/091; A61B 5/087

See application file for complete search history.

(56) References Cited

U.S. PATENT DOCUMENTS

| | | | | |
|---|---|---|---|---|
| 5,931,162 | A * | 8/1999 | Christian | A61M 16/024 128/204.18 |
| 6,920,875 | B1 * | 7/2005 | Hill | A61M 16/026 128/204.18 |
| 7,662,101 | B2 * | 2/2010 | Lee | A61B 5/0205 600/484 |
| 8,408,203 | B2 * | 4/2013 | Tham | A61M 16/0051 128/200.14 |
| 9,114,219 | B2 * | 8/2015 | Kimm | A61M 16/00 |
| 2006/0020295 | A1 * | 1/2006 | Brockway | A61B 5/02405 607/17 |
| 2010/0180897 | A1 * | 7/2010 | Malgouyres | A61M 16/024 128/204.23 |
| 2012/0060838 | A1 * | 3/2012 | Laura Lapoint | A61M 16/024 128/204.21 |
| 2014/0150791 | A1 * | 6/2014 | Birnkrant | A61M 16/0006 128/204.23 |

* cited by examiner

SYSTEM AND METHOD FOR CONTROLLING EXSUFFLATION PRESSURE DURING IN-EXSUFFLATION

CROSS-REFERENCE TO RELATED APPLICATIONS

This patent application claim the priority benefit under 35 U.S.C. § 371 of international patent application no. PCT/IB2014/064268, filed Sep. 5, 2014 which claims the priority benefit under 35 U.S.C. § 119(e) of U.S. Provisional Application No. 61/879,759 filed on Sep. 19, 2013, the contents of which are herein incorporated by reference.

BACKGROUND OF THE INVENTION

1. Field of the Invention

The present disclosure pertains to a system and method to in-exsufflate a subject.

2. Description of the Related Art

Coughing functions to clear mucus from the airway of a subject. Some people, due to injury, disease, or thoracic surgery, find it difficult or impossible to cough effectively on their own. For these people, assisted, or artificial, airway clearance is prescribed. One such method employs the use of mechanical in-exsufflation (MI-E). In-exsufflation is performed with a medical device that delivers positive airway pressure through the mouth, nose, or a tracheostomy, gently filling the lungs to capacity (insufflation). It then abruptly reverses pressure which generates an expiratory flow, mimicking a cough (exsufflation).

A significant population of patients with amyotrophica lateral sclerosis (ALS) depends on mechanical ventilation and/or mechanical in-exsufflation (MI-E) for secretion management. Many ALS patients lose muscle tone in the muscles of their upper airway. The lost muscle tone often causes in-exsufflation therapy to be ineffective on ALS patients because the upper airway of the patient collapses during the exsufflation cycle of the in-exsufflation therapy. Currently, there is no effective non-invasive treatment to manage airway secretion for patients, such as ALS patients, whose upper airway collapses during in-exsufflation therapy because of lost muscle tone.

SUMMARY OF THE INVENTION

Accordingly, one or more aspects of the present disclosure relate to a system configured to in-exsufflate a subject. The system comprises a pressure generator, one or more sensors, one or more processors, and/or other components. The pressure generator is configured to generate a pressurized flow of breathable gas for delivery to an airway of the subject. The one or more sensors are configured to generate output signals conveying information related to one or more parameters of the pressurized flow of breathable gas. The one or more processors are configured to execute computer program modules. The computer program modules comprise a control module, a target module, an exhalation module, a comparison module, an adjustment module, and/or other modules. The control module is configured to control the pressure generator according to an in-exsufflation therapy regime based on the output signals. The in-exsufflation therapy regime includes an exsufflation pressure of the pressurized flow of breathable gas during exhalation of the subject. The target module is configured to determine a target exhalation tidal volume for exhalations of the subject based on the output signals. The exhalation module is configured to determine actual exhalation tidal volume for exhalations of the subject based on the output signals. The comparison module is configured to compare the actual exhalation tidal volume to the target exhalation tidal volume. The adjustment module is configured to adjust the exsufflation pressure in the in-exsufflation therapy regime based on the comparison between the actual exhalation tidal volume and the target exhalation tidal volume.

Yet another aspect of the present disclosure relates to a method for inexsufflating a subject with an in-exsufflation system. The in-exsufflation system comprises a pressure generator, one or more sensors, one or more processors, and/or other components. The one or more processors are configured to execute computer program modules. The computer program modules comprise a control module, a target module, an exhalation module, a comparison module, an adjustment module, and/or other modules. The method comprises generating, with the pressure generator, a pressurized flow of breathable gas for delivery to an airway of the subject; generating, with the one or more sensors, output signals conveying information related to one or more parameters of the pressurized flow of breathable gas; controlling, with the control module, the pressure generator according to an in-exsufflation therapy regime based on the output signals, the in-exsufflation therapy regime including an exsufflation pressure of the pressurized flow of breathable gas during exhalation of the subject; determining, with the target module, a target exhalation tidal volume for exhalations of the subject based on the output signals; determining, with the exhalation module, actual exhalation tidal volume for exhalations of the subject based on the output signals; comparing, with the comparison module, the actual exhalation tidal volume to the target exhalation tidal volume; and adjusting, with the adjustment module, the exsufflation pressure in the in-exsufflation therapy regime based on the comparison between the actual exhalation tidal volume and the target exhalation tidal volume.

Still another aspect of the present disclosure relates to a system configured to in-exsufflate a subject. The system comprises means for generating a pressurized flow of breathable gas for delivery to an airway of the subject, means for generating output signals conveying information related to one or more parameters of the pressurized flow of breathable gas, and means for executing computer program modules. The computer program modules comprise means for controlling the pressure generator according to an in-exsufflation therapy regime based on the output signals. The in-exsufflation therapy regime includes an exsufflation pressure of the pressurized flow of breathable gas during exhalation of the subject. The computer program modules comprise means for determining a target exhalation tidal volume for exhalations of the subject based on the output signals. The computer program modules comprise means for determining actual exhalation tidal volume for exhalations of the subject based on the output signals. The computer program modules comprise means for comparing the actual exhalation tidal volume to the target exhalation tidal volume. The computer program modules comprise means for adjusting the exsufflation pressure in the in-exsufflation therapy regime based on the comparison between the actual exhalation tidal volume and the target exhalation tidal volume.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
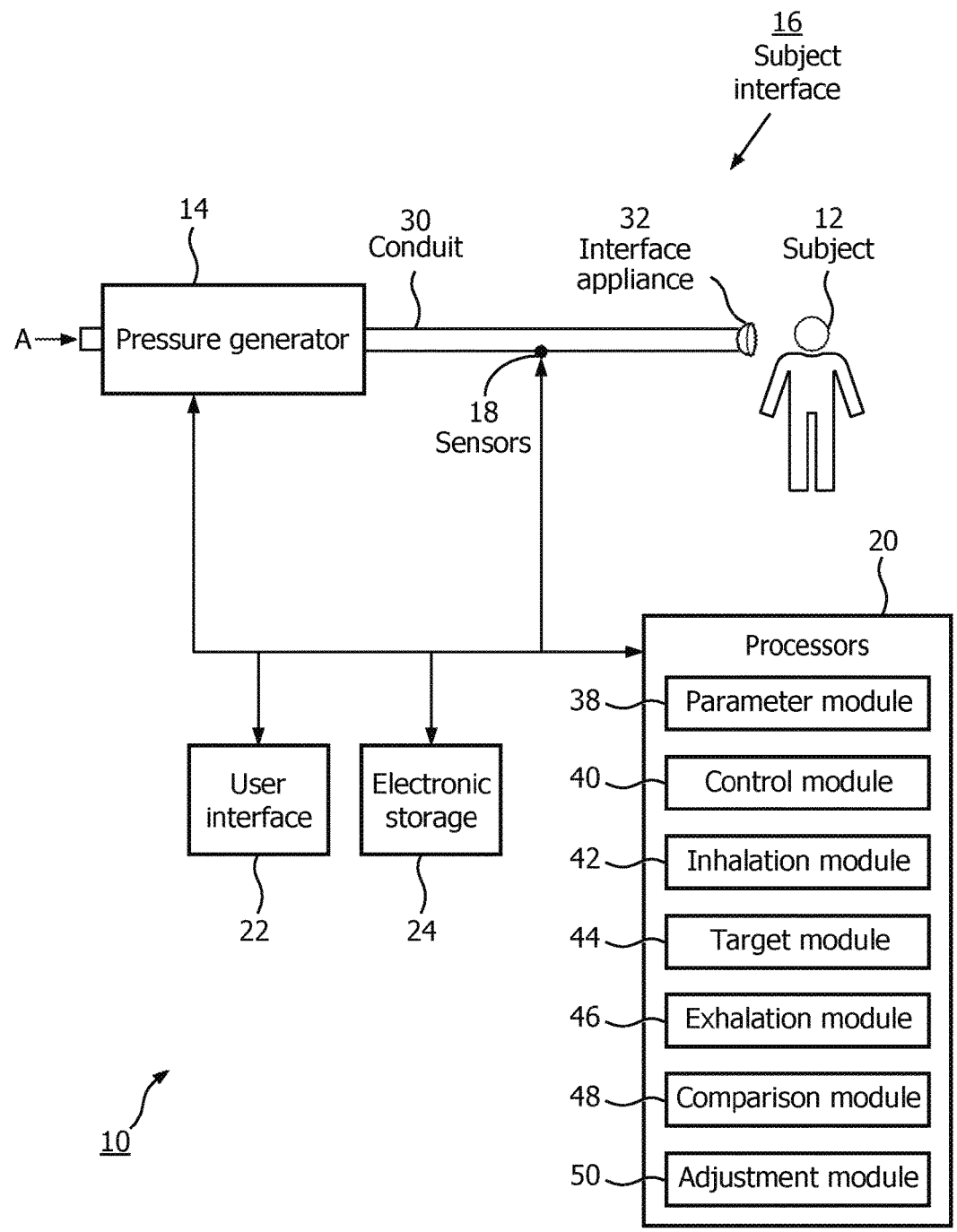
FIG. 1 schematically illustrates a system configured to in-exsufflate a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to insufflate and exsufflate (hereafter "in-exsufflate") a subject 12. System 10 provides an effective non-invasive alternative to invasive treatments such as a tracheostomy for ALS patients. System 10 detects airway collapse during exsufflation and adjusts in-exsufflation therapy settings to minimize airway collapse, thus maximizing the efficacy of the in-exsufflation therapy.

In some embodiments, tidal volume, tidal flow rate, and/or other parameters are monitored during in-exsufflation. Exsufflation pressure is adjusted based on the monitored parameters to maintain an open airway during exhalation of subject 12. Exsufflation pressure is adjusted based on a comparison of an actual exhalation tidal volume to a target exhalation tidal volume, an actual exhalation flow rate to a target exhalation flow rate, an actual inhalation tidal volume to a target inhalation tidal volume, and/or other comparisons. Responsive to a determination that a target exhalation tidal volume has not been reached, a target exhalation flow rate has not been reached, and/or a target inhalation tidal volume has not been reached, system 10 is configured to adjust the exsufflation pressure to maintain an open airway during exhalation of subject 12. In some embodiments, system 10 comprises one or more of a pressure generator 14, a subject interface 16, one or more sensors 18, a processor 20, a user interface 22, electronic storage 24, and/or other components.

Pressure generator 14 is configured to provide a pressurized flow of breathable gas for delivery to the airway of subject 12 (inflow to subject 12) and/or to draw gas from the airway (outflow from subject 12) of subject 12 (e.g., to exsufflate). Pressure generator 14 may be configured such that one or more gas parameters of the pressurized flow of breathable gas are controlled in accordance with an in-exsufflation therapy regime to in-exsufflate subject 12. The one or more gas parameters may include, for example, one or more of pressure, volume, flow rate, humidity, velocity, acceleration, and/or other parameters. In some embodiments, pressure generator 14 is a device dedicated to mechanical in-exsufflation. In some embodiments, pressure generator 14 is a ventilator and/or positive airway pressure device configured to provide therapy other than and/or in addition to in-exsufflation.

Pressure generator 14 receives a flow of gas from a gas source, such as the ambient atmosphere, as indicated by arrow A and elevates the pressure of that gas for delivery to the airway of a patient. Pressure generator 14 is any device, such as, for example, a pump, blower, piston, or bellows, that is capable of elevating the pressure of the received gas for delivery to a patient. The present disclosure also contemplates that gas other than ambient atmospheric air may be introduced into system 10 for delivery to the patient. In such embodiments, a pressurized canister or tank of gas containing air, oxygen, and/or another gas may supply the intake of pressure generator 14.

Pressure generator 14 may comprise one or more valves for controlling the pressure and/or flow direction of gas in pressure generator 14, a manifold defining the gas flow path in pressure generator 14, and/or other components. The present disclosure also contemplates controlling the operating speed of the blower, for example, either alone or in combination with such valves and/or the manifold, to control the pressure/flow of gas provided to and/or drawn from the patient.

By way of a non-limiting example, pressure generator 14 may be configured to adjust the parameters of the pressurized flow of breathable gas in accordance with an in-exsufflation therapy regime. In one embodiment, the therapy regime may dictate that the pressurized flow of breathable gas is delivered to the airway of subject 12 at a first pressure level during insufflation. The first pressure level is sufficiently high enough that the lungs of subject 12 are at least partially filled during insufflation. After insufflation, pressure generator 14 may reduce the pressure of the pressurized flow of breathable gas with sufficient abruptness that expiratory flow through the airway of subject 12 is sufficient to remove mucus and/or other debris from the airway and/or lungs of subject 12. The pressure may be reduced from the first pressure level to a second pressure level that is substantially lower than the first pressure level. The second pressure level may, for example, be a negative pressure, below atmospheric pressure. After expiration is complete, pressure generator 14 may return the pressure of the pressurized flow of breathable gas to the first pressure level to facilitate another inspiration in preparation for another in-exsufflation. After a series of in-exsufflations, in-exsufflation may be ceased.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is configured to be removably coupled with conduit 30 and/or other conduits and/or interface appliances being used to deliver respiratory therapy to subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. In some embodiments, interface appliance 32 is invasive. Some examples of invasive interface appliances that may comprise interface appliance 32 are endotracheal tubes, tracheostomy tubes, and or other devices. The present disclosure is not limited to these examples, and contemplates delivery of the flow of gas to the subject using any interface appliance.

Although subject interface 16 is illustrated in FIG. 1 as a single-limbed interface for the delivery of the flow of gas to the airway of the subject, this is not intended to be limiting. The scope of this disclosure comprises double-limbed circuits having a first limb configured to both provide the flow of gas to the airway of the subject, and a second limb configured to selectively exhaust gas (e.g., to exhaust exhaled gases).

Sensors 18 are configured to generate output signals conveying information related to one or more parameters of the pressurized flow of breathable gas. The parameters may include parameters related to gas within subject interface 16 and/or other components of system 10, parameters related to the respiration of subject 12, parameters related to the in-exsufflation therapy regime, and/or other parameters. For example, the one or more parameters may include one or more of a flow rate, a volume, a pressure, a composition (e.g., concentration(s) of one or more constituents), a temperature, a humidity, an acceleration, a velocity, and/or other parameters. In some embodiments, sensors 18 include a volume sensor, a flow rate sensor, a pressure sensor and/or other sensors.

Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters), and/or other information. Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 38, a control module 40, an inhalation module 42, a target module 44, an exhalation module 46, a comparison module 48, an adjustment module 50, and/or other modules. Processor 20 may be configured to execute modules 38, 40, 42, 44, 46, 48, and/or 50 by software; hardware; firmware; some combination of software, hardware, and/or firmware; and/or other mechanisms for configuring processing capabilities on processor 20.

It should be appreciated that although modules 38, 40, 42, 44, 46, 48, and/or 50 are illustrated in FIG. 1 as being co-located within a single processing unit, in implementations in which processor 20 comprises multiple processing units, one or more of modules 38, 40, 42, 44, 46, 48, and/or 50 may be located remotely from the other modules. The description of the functionality provided by the different modules 38, 40, 42, 44, 46, 48, and/or 50 described below is for illustrative purposes, and is not intended to be limiting, as any of modules 38, 40, 42, 44, 46, 48, and/or 50 may provide more or less functionality than is described. For example, one or more of modules 38, 40, 42, 44, 46, 48, and/or 50 may be eliminated, and some or all of its functionality may be provided by other modules 38, 40, 42, 44, 46, 48, and/or 50. As another example, processor 20 may be configured to execute one or more additional modules that may perform some or all of the functionality attributed below to one of modules 38, 40, 42, 44, 46, 48, and/or 50.

Parameter module 38 is configured to determine one or more parameters within system 10. The one or more parameters within system 10 may comprise gas parameters related to the pressurized flow of breathable gas, breathing parameters related to the respiration of subject 12, parameters related to the in-exsufflation therapy, and/or other parameters. Parameter module 38 is configured to determine the one or more parameters based on the output signals of sensors 18, and/or other information. The information determined by parameter module 38 may be used by control module 40 for controlling pressure generator 14, used by other modules of processor 20, stored in electronic storage 24, displayed by user interface 22, and/or used for other purposes. The one or more parameters determined by parameter module 38 may comprise, for example, one or more of a flow rate, a volume, a pressure, a composition (e.g., concentration(s) of one or more constituents), a temperature, a humidity, an acceleration, a velocity, and/or other parameters.

Control module 40 is configured to control pressure generator 14 according to an in-exsufflation therapy regime. Control module 40 is configured to control pressure generator 14 based on the output signals from sensors 18, information determined by parameter module 38, information entered and/or selected by a user via user interface 22, and/or other information. In some embodiments, the in-exsufflation therapy regime may specify an insufflation pressure that control module 40 causes pressure generator 14 to maintain during inhalation of subject 12, an exsufflation pressure that control module 40 causes pressure generator 14 to maintain during exhalation of subject 12, and/or other parameters of the pressurized flow of breathable gas.

In some embodiments, control module 40 is configured to control pressure generator 14 to reduce the pressure of the pressurized flow of breathable gas for exsufflation compared to the pressure during insufflation with sufficient abruptness that expiratory flow through the airway of subject 12 is sufficient to remove mucus and/or other debris from the airway and/or lungs of subject 12. For example, the in-exsufflation therapy regime may dictate that the pressurized flow of breathable gas be delivered to the airway of subject 12 at an insufflation pressure during inhalation of about 40 cm $H_2O$, and an exsufflation pressure during exhalation of about −40 cm $H_2O$.

In some embodiments, control module 40 is configured to control pressure generator 14 to generate the flow of gas in accordance with a ventilator and/or positive airway pressure therapy regime instead of, and/or in addition to, the in-exsufflation therapy regime described above. For example, control module 40 may control pressure generator 14 such that the pressure support provided to the subject via the flow of gas comprises non-invasive ventilation, positive airway pressure support, continuous positive airway pressure support, bi-level support, BiPAP®, and/or other types of pressure support therapy. In this example, subject 12 may trigger pressure generator 14 to switch from an airway pressure support operation regime to the in-exsufflation therapy regime and/or to switch from the in-exsufflation therapy regime to the airway pressure support regime. Subject 12 may trigger the switch from one operation regime to the other via user interface 22, and/or by other methods.

Inhalation module 42 is configured to determine an actual inhalation tidal volume for inhalations of subject 12. Inhalation module 42 may be configured to determine an actual inhalation tidal volume for individual sets of inhalations of subject 12. Such a set of inhalations may include a single inhalation or multiple inhalations. Inhalation module 42 may be configured to determine actual inhalation tidal volume based on the output signals of sensors 18 (e.g., direct measurement of the volume), based on the flow rate (e.g., determined by parameter module 38) of the pressurized flow of breathable gas during inhalation, and/or based on other information.

Figure 2:
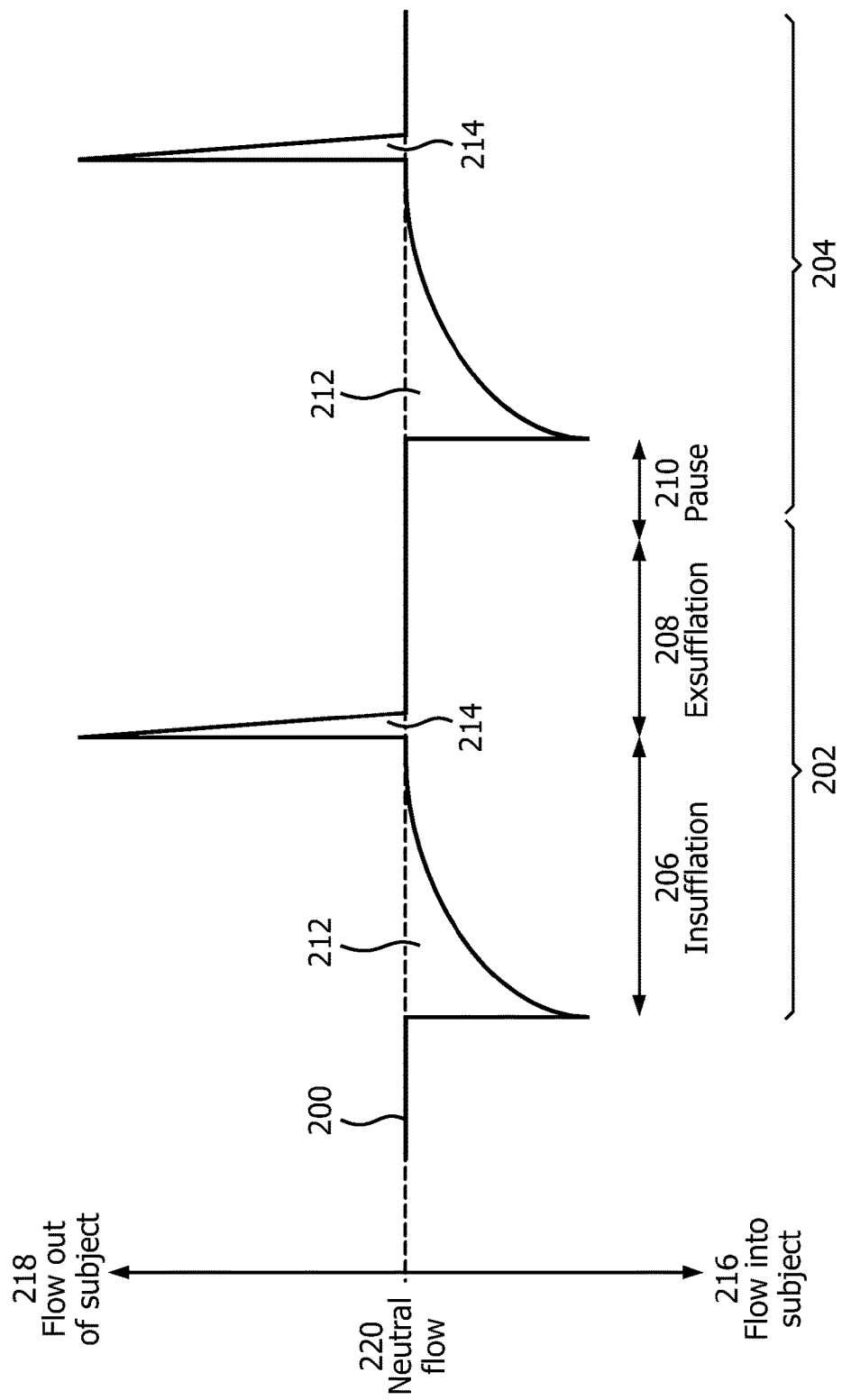
FIG. 2 illustrates a baseline flow rate waveform of the pressurized flow of breathable gas for two respiratory cycles during in-exsufflation therapy.

For example, FIG. 2 illustrates a baseline flow rate waveform 200 of the pressurized flow of breathable gas for two respiratory cycles 202, 204 during in-exsufflation therapy. In-exsufflation therapy includes insufflation 206, exsufflation 208, and a pause 210. Flow rate waveform 200 may result from, for example, a baseline in-exsufflation therapy regime that includes an insufflation pressure of +40cm$H_2O$ (resulting in flow 216 into the subject) and an exsufflation pressure of −40cm$H_2O$ (resulting in flow 218 out of the subject). An area 212 formed by flow rate waveform 200 and neutral flow indicator 220 during insufflation 206 represents the actual inhalation tidal volume for the inhalation of subject 12. The size of area 212 (e.g., the actual inhalation tidal volume) may be determined based on an integration of flow rate waveform 200 during insufflation 206, for example. The inhalation volume can be calculated, for example, by performing a definite integral function of the flow rate waveform over the interval of the predefined insufflation time.

Returning to FIG. 1, target module 44 is configured to determine a target exhalation tidal volume for exhalation of subject 12. Target module 44 is configured to determine the target volume based on one or more of the output signals from sensors 18, the parameters determined by parameter module 38, the actual inhalation tidal volume determined by inhalation module 42, information obtained via user interface 22 (e.g., entry and/or selection of a target exhalation tidal volume by a user), and/or other information. In some embodiments, target module 44 may be configured to determine the target exhalation tidal volume based on a known vital capacity of subject 12. The known vital capacity may be previously determined based on one or more standardized physiological tests performed on subject 12. For example, spirometry is the most commonly performed and universally accepted standard pulmonary function test. The test outcome is unique to individual. The vital capacity can be measured using a spirometer in which the subject inhales maximally and then exhales as completely as possible. The known vital capacity may be entered and/or selected by subject 12 and/or other users via user interface 22, for example.

In some embodiments, target module 44 is configured to determine a target exhalation tidal volume for individual sets of exhalations of subject 12. Such a set of exhalations may include a single exhalation or multiple exhalations. The target exhalation tidal volume for a set of exhalations may be different than and/or the same as one or more previously determined target exhalation tidal volumes. In some embodiments, a set of exhalations that includes multiple exhalations may include consecutive exhalations.

In embodiments where target module 44 is configured to determine the target exhalation tidal volume based on the actual inhalation tidal volume determined by inhalation module 42, the target exhalation tidal volume may correspond to the actual inhalation tidal volume determined by inhalation module 42. The target exhalation tidal volume may be a pre-determined portion of the actual inhalation tidal volume. For example, the target exhalation tidal volume may be about 50% of the actual inhalation tidal volume. The target exhalation tidal volume may be about 40% of the actual inhalation tidal volume. The target exhalation tidal volume may be 60% of the actual inhalation tidal volume. The target exhalation tidal volume may be between about 30% and about 70% of the actual inhalation tidal volume. The target exhalation tidal volume may be about 30% or more of the actual inhalation tidal volume. The pre-determined portion may be determined at manufacture, set and/or adjusted by subject 12 and/or other users via user interface 22, determined based on previous respiration of subject 12, and/or determined by other methods. In some embodiments, the target exhalation tidal volume may be determined based on an average and/or other combination of two or more previously determined actual inhalation tidal volumes from two or more inhalations of subject 12.

Exhalation module 46 is configured to determine actual exhalation tidal volume for exhalations of subject 12. Exhalation module 46 may be configured to determine an actual exhalation tidal volume for individual exhalations of subject 12. Exhalation module 46 is configured to determine actual exhalation tidal volume based on the outputs signals of sensors 18 (e.g., direct measurement of the volume), based on the flow rate (e.g., determined by parameter module 38) of the pressurized flow of breathable gas during exhalation, and/or based on other information. Returning to the example shown in FIG. 2, an area 214 formed by flow rate waveform 200 and neutral flow indicator 220 during exsufflation 208 represents the actual exhalation tidal volume for the exhalation of subject 12. The size of area 214 (e.g., the actual exhalation tidal volume) may be determined based on an integration of flow rate waveform 200 during exsufflation 208, for example. In the example shown in FIG. 2, area 214 is significantly (e.g., more than 50%) smaller than area 212.

Returning to FIG. 1, comparison module 48 is configured to compare the actual exhalation tidal volume to the target exhalation tidal volume. Comparing the actual exhalation tidal volume to the target exhalation tidal volume may include comparing physical volume levels (e.g. comparing a first quantity of liters to a second quantity of liters), comparing areas 212 and 214 (shown in FIG. 2), and/or other comparisons. In some embodiments, comparison module 48 is configured to compare the actual exhalation tidal volume to the target exhalation tidal volume after subject 12 has fully exhaled. In some embodiments, comparison module 48 is configured to compare a current actual exhalation tidal volume (e.g., the current total volume of gas exhaled since the start of a given exhalation) to the target exhalation tidal volume one or more times during an individual exhalation.

Adjustment module 50 is configured to adjust the exsufflation pressure in the in-exsufflation therapy regime based on the comparison between the actual exhalation tidal volume and the target exhalation tidal volume. Adjusting may include increasing the exsufflation pressure, decreasing the exsufflation pressure, and/or keeping the exsufflation pressure the same. In some embodiments, responsive to a comparison by comparison module 48 indicating that an actual exhalation tidal volume did not reach a target exhalation tidal volume during a given exhalation, adjustment module 50 is configured to increase the exsufflation pressure for one or more exhalations subsequent to the given exhalation. The actual exhalation tidal volume not reaching the target exhalation tidal volume during a given exhalation may indicate that the airway of subject 12 collapsed and/or closed significantly (e.g., such that a quantity of gas is prevented from being exhaled by subject 12 due to the significant closure). Adjustment module 50 may adjust the exsufflation pressure of the in-exsufflation therapy regime to ensure that the airway of subject 12 remains open during exsufflation.

For example, target module 44 may determine a first target exhalation tidal volume based on a first actual inhalation tidal volume during a first inhalation. The first actual inhalation tidal volume may be determined by inhalation module 42. Responsive to a first comparison by comparison module 48 indicating that a first actual exhalation tidal volume (e.g., determined by exhalation module 46) did not reach the first target exhalation tidal volume during a first exhalation, adjustment module 50 may be configured to increase the exsufflation pressure by about 5 cmH$_2$O (e.g., from −40cmH$_2$O to about −35cmH$_2$O) for at least a second exhalation. (It should be noted that the term "increase" is not intended to be limiting. In this example, numerically speaking the adjustment is an increase. The "increase" described here corresponds to a reduction in a force due to the "increased" exsufflation pressure.)

Responsive to a second comparison by comparison module 48 indicating that a second target exhalation tidal volume (e.g., determined as described above based on a second inhalation that followed the first exhalation) was not reached during the second exhalation, adjustment module 50 may be configured to increase the exsufflation pressure another 5 cmH$_2$O (e.g., from about −35cmH$_2$O to about −30H$_2$O) for the next exhalation. The two 5 cmH$_2$O adjustments by adjustment module 50 in the example above are not intended to be limiting. In some embodiments, adjustment module 50 may be configured to increase the exsufflation pressure by about 10 cmH$_2$O. In some embodiments, adjustment module 50 may be configured to increase the exsufflation pressure by about 20 cmH$_2$O. In some embodiments, adjustment module 50 may be configured to increase the exsufflation pressure between about 5 cmH$_2$O and about 40cmH$_2$O. In some embodiments, adjustment module 50 may be configured to increase the exsufflation pressure by up to about 40cmH$_2$O.

Adjustment module 50 is configured to cease increasing the exsufflation pressure for subsequent exhalations responsive to the comparison by comparison module 48 indicating that the actual exhalation tidal volume reached the target exhalation tidal volume during a given exhalation. Returning to the example above, if the second comparison by comparison module 48 indicated that the target exhalation tidal volume was reached during the second exhalation, adjustment module 50 may be configured to keep the −30cmH$_2$O exsufflation pressure the same during subsequent exhalations.

In some embodiments, adjustment module 50 may be configured to continue increasing the exsufflation pressure for subsequent exhalations as described above until an exsufflation pressure maximum is reached. The exsufflation pressure maximum may be determined at manufacture, determined based on previous respiration of subject 12, obtained via information entered and/or selected by subject 12 and/or other users via user interface 22, and/or determined by other methods.

Figure 3:
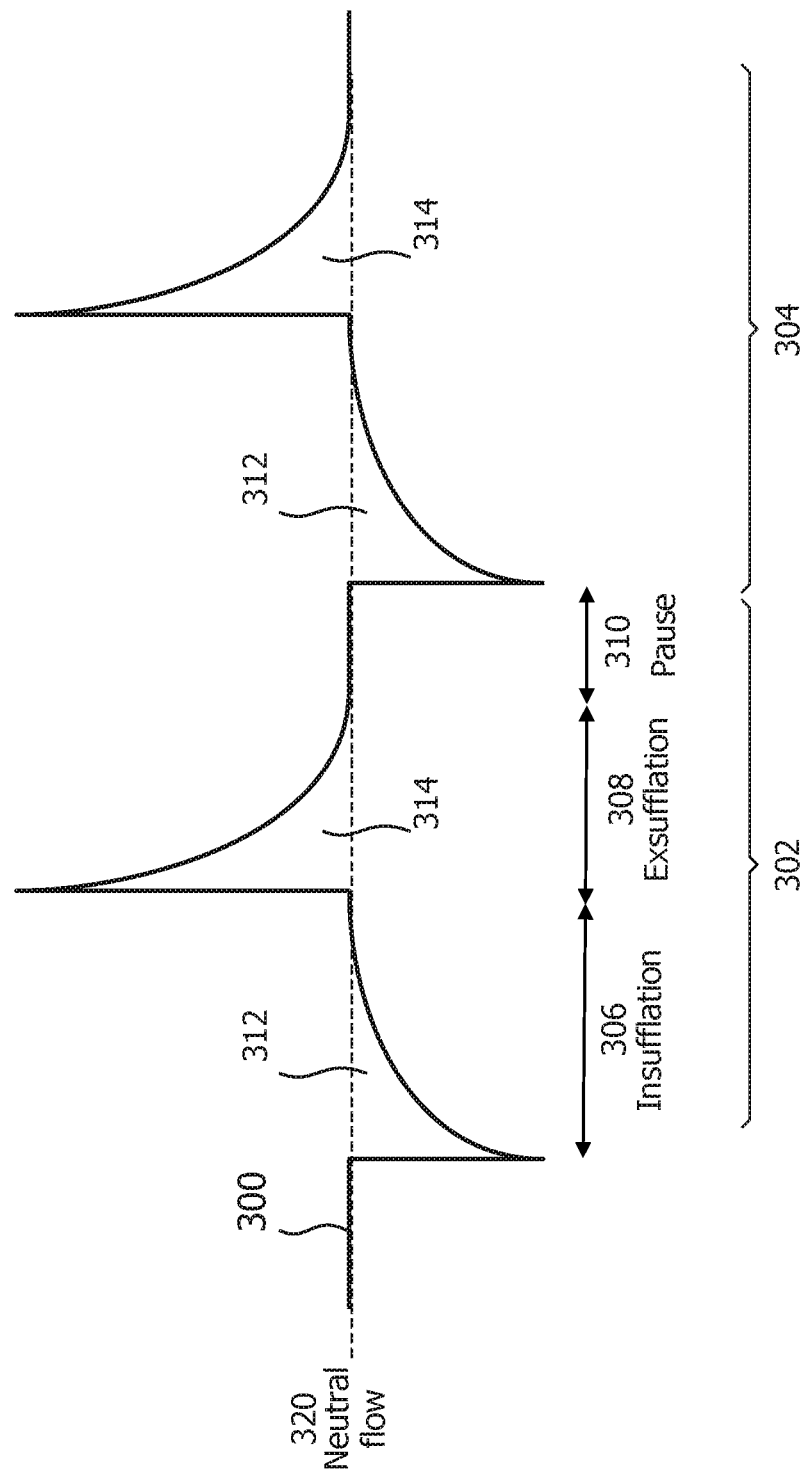
FIG. 3 illustrates an adjusted flow rate waveform of the pressurized flow of breathable gas for two respiratory cycles during in-exsufflation therapy.

By way of a non-limiting example, FIG. 3 illustrates an adjusted flow rate waveform 300 of the pressurized flow of breathable gas for two respiratory cycles 302, 304 during in-exsufflation therapy. In the examples shown in FIG. 2 and FIG. 3, a target exhalation tidal volume of at least 50% (for example) of the actual inhalation tidal volume (e.g., area 212 in FIG. 2) may have been determined by target module 44 (shown in FIG. 1). A comparison by comparison module 48 (FIG. 1) of the sizes of areas 214 (the actual exhalation tidal volume) and 212 (the actual inhalation tidal volume) may indicate that area 214 is smaller than area 212 by more than 50% (e.g., the actual exhalation tidal volume did not reach the target exhalation tidal volume). The more than 50% smaller size of area 214 compared to area 212 may indicate that the airway of subject 12 (FIG. 1) closed during exsufflation 208.

Responsive to the comparison by comparison module 48 indicating that the target exhalation tidal volume was not reached during the exhalation, adjustment module 50 (FIG. 1) may be configured to increase the exsufflation pressure for one or more exhalations subsequent to the given exhalation. As shown in FIG. 3, adjusted flow rate waveform 300 may result from, for example, adjusting the baseline in-exsufflation therapy regime (e.g., insufflation pressure of +40cmH$_2$O and exsufflation pressure of −40cmH$_2$O) by increasing the exsufflation pressure from −40cmH$_2$O to −20cmH$_2$O for respiratory cycle 302 and 304. In FIG. 3, an area 312 formed by adjusted flow rate waveform 300 and neutral flow indicator 320 during insufflation 306 is similar in size compared to an area 314 formed by adjusted flow rate waveform 300 and neutral flow indicator 320 during exsufflation 308. The similar sizes of areas 312 and 314 may indicate that the airway of subject 12 (FIG. 1) remained open during exsufflation 308.

Returning to FIG. 1, in some embodiments, system 10 may be configured to adjust the exsufflation pressure based on one or more parameters in addition to and/or instead of the actual inhalation tidal volume (from which target module 44 determines the target exhalation tidal volume) and/or the actual exhalation tidal volume. For example, in some embodiments, target module 44 is configured to determine a target inhalation tidal volume, a target exhalation flow rate, and/or other target parameters for exhalations of subject 12 (e.g., in addition to and/or instead of a target exhalation tidal volume). Target module 44 may be configured to determine the target inhalation tidal volume, the target exhalation flow rate, and/or other target parameters based on the output signals from sensors 18, the parameters determined by parameter module 38, information entered and/or selected by users via user interface 22, and/or based on other information.

In some embodiments, comparison module 48 is configured to compare the actual inhalation tidal volume to the target inhalation tidal volume, compare an actual exhalation flow rate during exhalation of subject 12 to the target exhalation flow rate, and/or make other comparisons. Adjustment module 50 is configured to adjust the exsufflation pressure of the in-exsufflation therapy regime based on the comparison between the actual inhalation tidal volume and the target inhalation tidal volume, the comparison between the actual exhalation flow rate and the target exhalation flow rate, and/or the other comparisons.

For example, an actual inhalation tidal volume not reaching a target inhalation tidal volume may indicate that subject 12 was not able to fully inhale because he or she had not fully exhaled during a previous exhalation. In this example, target module 44 may determine a target inhalation tidal volume for a second inhalation based on an actual inhalation tidal volume from a first inhalation (determined by inhalation module 42). The actual inhalation tidal volume for the second inhalation may be compared to the target inhalation tidal volume for the second inhalation by comparison module 48. Responsive to the comparison by comparison module 48 indicating that the target inhalation tidal volume for the second inhalation was not reached, adjustment module 50 may be configured to increase the exsufflation pressure for one or more exhalations subsequent to the second inhalation.

Figure 4:
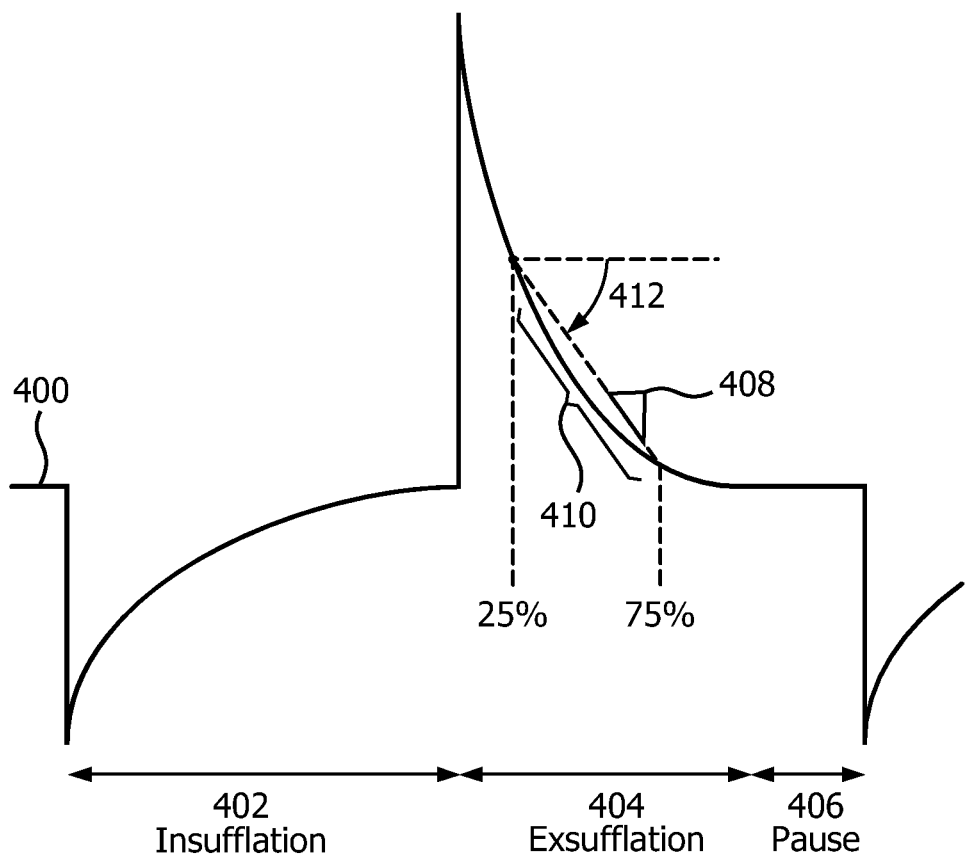
FIG. 4 illustrates a flow rate waveform during insufflation, exsufflation, and a pause.

As another example, FIG. 4 illustrates a flow rate waveform 400 during insufflation 402, exsufflation 404, and a pause 406. Comparison module 48 (FIG. 1) may be configured to compare a slope 408 from a portion 410 of flow rate waveform 400 during exsufflation 404 to a flow rate waveform slope target. The flow rate waveform slope target may be determined by target module 44, for example. The flow rate waveform slope target may be determined at manufacture, determined by target module 44 via entries and/or selections made by subject 12 and/or other users via user interface 22, determined by target module 44 based on previous respiration of subject 12, and/or determined by other methods. In some embodiments, the flow rate waveform slope target may correspond to, for example, a declination angle 412 of about 85° or less. In some embodiments, the flow rate waveform slope target may correspond to a declination angle 412 of about 70° or less. In some embodiments, the flow rate waveform slope target may correspond to a declination angle 412 of about 60° or less. In some embodiments, the flow rate waveform slope target may correspond to a declination angle 412 of about 45° or less. In some embodiments, the flow rate waveform slope target may correspond to a declination angle 412 of between about 45° and about 85°.

In some embodiments, comparison module 48 may determine slope 408 of a portion 410 of waveform 400 between about 25% of a completed exhalation and about 75% of a completed exhalation as shown in FIG. 4. The portion 410 of waveform 400 between about 25% and about 75% is not intended to be limiting. Any portion of waveform 400 during exsufflation 404 may be used by comparison module 48 to determine slope 408 that allows system 10 to function as described herein. Responsive to the comparison by comparison module 48 indicating that the flow rate waveform slope target was not reached, adjustment module 50 may be configured to increase the exsufflation pressure for one or more subsequent exhalations. The flow rate waveform slope not reaching the flow rate waveform target may indicate that the exhalation of subject 12 ended quickly and subject 12 was not able to fully exhale because his or her airway closed during exhalation.

Returning to FIG. 1, user interface 22 is configured to provide an interface between system 10 and subject 12 and/or other users through which subject 12 and/or other users may provide information to and receive information from system 10. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 5:
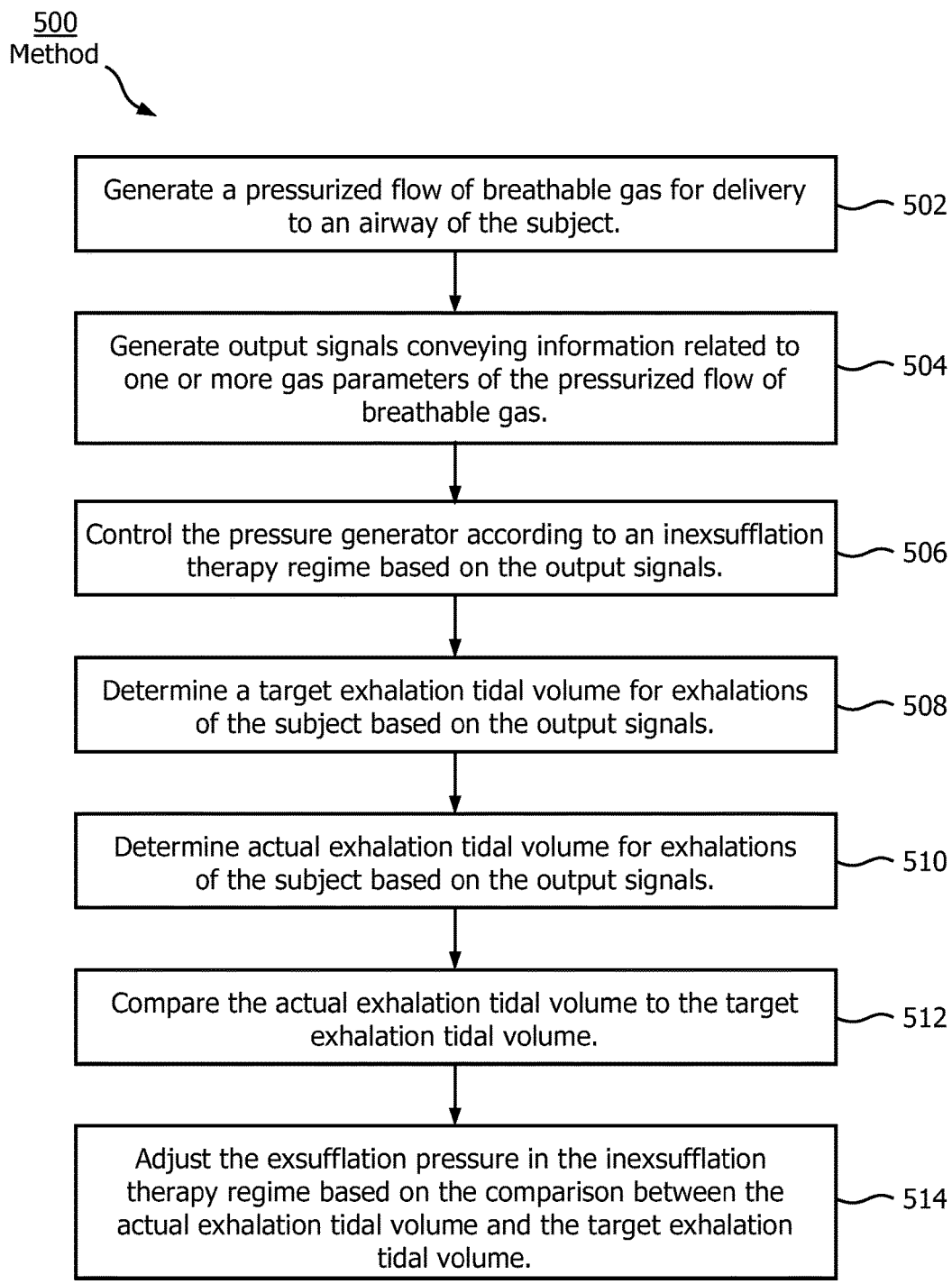
FIG. 5 illustrates a method to in-exsufflate a subject.

FIG. 5 illustrates a method 500 of inexsufflating a subject with an in-exsufflation system. The in-exsufflation system comprises a pressure generator, one or more sensors, one or more processors, and/or other components. The one or more processors are configured to execute computer program modules. The computer program modules comprise a control module, a target module, an exhalation module, a comparison module, an adjustment module, and/or other modules. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a pressurized flow of breathable gas for delivery to the airway of a subject is generated. In some embodiments, operation 502 is performed by a pressure generator the same as or similar to pressure generator 14 (shown in FIG. 1 and described herein).

At an operation 504, output signals are generated conveying information related to one or more parameters of the pressurized flow of breathable gas. In some embodiments, operation 504 is performed by sensors the same as or similar to sensors 18 (shown in FIG. 1 and described herein).

At an operation 506, the pressure generator is controlled according to an in-exsufflation therapy regime. The pressure generator is controlled based on the output signals. The in-exsufflation therapy regime includes an exsufflation pressure of the pressurized flow of breathable gas that is delivered during exhalation of the subject. In some embodiments, operation 506 is performed by a processor module the same as or similar to control module 40 (shown in FIG. 1 and described herein.)

At an operation 508, a target exhalation tidal volume is determined. The target exhalation tidal volume is determined for exhalations of the subject. The target exhalation tidal volume is determined based on the output signals. In some embodiments, the target exhalation tidal volume may be determined based on an actual inhalation tidal volume. The actual inhalation tidal volume may be determined by a computer program module the same as or similar to inhalation module 42. Inhalation module 42 may determine the actual inhalation tidal volume based on the output signals. In some embodiments, operation 508 is performed by a processor module the same as or similar to target module 44 (shown in FIG. 1 and described herein.)

In some embodiments, in addition to, and/or instead of, determining a target exhalation tidal volume, target module 44 may determine a target inhalation tidal volume, a target exhalation flow rate, and/or other parameter targets for inhalation and/or exhalation.

At an operation 510, actual exhalation tidal volume for exhalations of the subject is determined. In some embodiments, the actual inhalation tidal volume, an actual exhalation flow rate, and/or other parameters may be determined in addition to, and/or instead of the actual exhalation tidal volume. The actual exhalation tidal volume, actual inhalation tidal volume, and the actual exhalation flow rate are determined based on the output signals. In some embodiments, operation 510 (e.g. determining the actual exhalation tidal volume and the actual exhalation flow rate) is performed by a processor module the same as or similar to exhalation module 46 (shown in FIG. 1 and described herein.) In some embodiments, operation 510 (e.g., determining the actual inhalation tidal volume) may be performed by inhalation module 42.

At an operation 512, the actual exhalation tidal volume is compared to the target exhalation tidal volume, the actual inhalation tidal volume is compared to the target inhalation tidal volume, and/or the actual exhalation flow rate is compared to the target exhalation flow rate. In some embodiments, operation 512 is performed by a processor module the same as or similar to comparison module 48 (shown in FIG. 1 and described herein).

At an operation 514, the exsufflation pressure in the in-exsufflation therapy regime is adjusted based on the comparison between the actual exhalation tidal volume and the target exhalation tidal volume, the comparison between the actual inhalation tidal volume and the target inhalation tidal volume, and/or the comparison between the actual exhalation flow rate and the target exhalation flow rate. In some embodiments, responsive to the comparison by the comparison module indicating that the target exhalation tidal volume, the target inhalation tidal volume, and/or the target exhalation flow rate has not been reached during a given inhalation and/or exhalation, the exsufflation pressure may be increased for one or more exhalations subsequent to the given inhalation and/or exhalation. In some embodiments, operation 514 is performed by a processor module the same as or similar to adjustment module 50 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to reduce airway collapse in a subject during in-exsufflation therapy, the system comprising:
    a pressure generator configured to generate a pressurized flow of breathable gas for delivery to an airway of the subject;
    one or more sensors configured to generate output signals conveying information related to one or more parameters of the pressurized flow of breathable gas; and
    one or more processors configured by machine readable instructions to:
        control the pressure generator based on an in-exsufflation therapy regime and the output signals to apply the pressurized flow of breathable gas, the in-exsufflation therapy regime including an exsufflation pressure of the pressurized flow of breathable gas during exhalation of the subject;
        determine, based on a percentage of an actual inhalation tidal volume of the subject during a first respiratory cycle, a target exhalation tidal volume for exhalation of the subject during a second respiratory cycle, the percentage being less than 100%;
        monitor, based on the output signals, an actual exhalation tidal volume of the subject during the second respiratory cycle;
        detect, based on the monitoring, an airway collapse of the subject, the detection of the airway collapse being based on a comparison of the actual exhalation tidal volume and the target exhalation tidal volume during the second respiratory cycle; and
        responsive to the detection of the airway collapse, adjust the control of the pressure generator by adjusting the exsufflation pressure in the in-exsufflation therapy regime.

2. The system of claim 1, wherein the detection of the airway collapse is responsive to the actual exhalation tidal volume not reaching the target exhalation tidal volume during the second respiratory cycle.

3. The system of claim 1, wherein the one or more processors are further configured to:
    determine a target inhalation tidal volume for the subject during the second respiratory cycle based on the actual inhalation tidal volume during the first respiratory cycle;
    monitor, based on the output signals, the actual inhalation tidal volume of the subject during the second respiratory cycle; and
    adjust the exsufflation pressure in the in-exsufflation therapy regime responsive to the actual inhalation tidal volume during the second respiratory cycle not reaching the target inhalation tidal volume.

4. The system of claim 1, wherein, responsive to the detection of the airway collapse, the one or more processors is configured to increase the exsufflation pressure for one or more exhalations during one or more respiratory cycles subsequent to the second respiratory cycle.

5. The system of claim 1, wherein the percentage is between about 30% and 70%.

6. A method to reduce airway collapse in a subject during in-exsufflation therapy the method comprising:
    generating, with a pressure generator, a pressurized flow of breathable gas for delivery to an airway of the subject;
    generating, with one or more sensors, output signals conveying information related to one or more parameters of the pressurized flow of breathable gas;
    controlling, with one or more processors, the pressure generator based on an in-exsufflation therapy regime and the output signals to apply the pressurized flow of breathable gas, the in-exsufflation therapy regime including an exsufflation pressure of the pressurized flow of breathable gas during exhalation of the subject;
    determining, with the one or more processors, based on a percentage of an actual inhalation tidal volume of the subject during a first respiratory cycle, a target exhalation tidal volume for exhalation of the subject during a second respiratory cycle, the percentage being less than 100%;
    monitoring, with the one or more processors, based on the output signals, an actual exhalation tidal volume of the subject during the second respiratory cycle;
    detecting, with the one or more processors, based on the monitoring, an airway collapse of the subject, the detection of the airway collapse being based on a comparison of the actual exhalation tidal volume and the target exhalation tidal volume during the second respiratory cycle; and
    responsive to the detection of the airway collapse, adjusting, with the one or more processors, the control of the pressure generator by adjusting the exsufflation pressure in the in-exsufflation therapy regime.

7. The method of claim 6, wherein the detection of the airway collapse is responsive to the actual exhalation tidal volume not reaching the target exhalation tidal volume during the second respiratory cycle.

8. The method of claim 6, further comprising:
    determining, with the one or more processors, a target inhalation tidal volume for the subject during the second respiratory cycle based on the actual inhalation tidal volume during the first respiratory cycle;
    monitoring, with the one or more processors, the actual inhalation tidal volume to the target inhalation tidal volume; and
    adjusting, with the one or more processors, the exsufflation pressure in the in-exsufflation therapy regime responsive to the actual inhalation tidal volume during the second respiratory cycle not reaching the target inhalation tidal volume.

9. The method of claim 6, further comprising, responsive to the detection of the airway collapse, increasing, with the one or more processors, the exsufflation pressure for one or more exhalations during one or more respiratory cycles subsequent to the second respiratory cycle.

10. The method of claim 6, wherein the percentage is between about 30% and 70% wherein the target exhalation tidal volume for exhalation of the subject during a second respiratory cycle is determined based on a percentage of about 30% and 70% of the actual inhalation tidal volume of the subject during a first respiratory cycle.

11. A system configured to reduce airway collapse in a subject during in-exsufflation therapy, the system comprising:
    means for generating a pressurized flow of breathable gas for delivery to an airway of the subject;

means for generating output signals conveying information related to one or more parameters of the pressurized flow of breathable gas;

means for controlling the means for generating a pressurized flow of breathable gas based on an in-exsufflation therapy regime to apply the pressurized flow of breathable gas, the in-exsufflation therapy regime including an exsufflation pressure of the pressurized flow of breathable gas during exhalation of the subject;

means for determining, based on an actual inhalation tidal volume of the subject during a first respiratory cycle, a target exhalation tidal volume for exhalations of the subject during a second respiratory cycle;

means for monitoring, based on the output signals, an actual exhalation tidal volume for exhalations of the subject during the second respiratory cycle;

means for detecting, based on the monitoring, an airway collapse in the subject, the detection of the airway collapse being based on a comparison of the actual exhalation tidal volume and the target exhalation tidal volume during the second respiratory cycle; and means for adjusting, responsive to the detection of the airway collapse, the control of the pressure generator by adjusting the exsufflation pressure in the in-exsufflation therapy regime.

12. The system of claim 11, wherein the detection of the airway collapse is responsive to the actual exhalation tidal volume not reaching the target exhalation tidal volume during the second respiratory cycle.

13. The system of claim 11, wherein:

the means for determining a target is configured to determine a target inhalation tidal volume for the subject during the second respiratory cycle based on the actual inhalation tidal volume during the first respiratory cycle;

the means for monitoring is configured to monitor the actual inhalation tidal volume during the second respiratory cycle; and adjust the exsufflation pressure in the in-exsufflation therapy regime responsive to the actual inhalation tidal volume during the second respiratory cycle not reaching the target inhalation tidal volume.

14. The system of claim 11, wherein responsive to the detection of the airway collapse, the means for processing is configured to increase the exsufflation pressure for one or more exhalations during one or more respiratory cycles subsequent to the second respiratory cycle.

15. The system of claim 11, wherein the target is determined based on a percentage of the actual inhalation tidal volume of the subject during the first respiratory cycle, the percentage being between about 30% and 70%.

* * * * *